United States Patent [19]

Matsuda et al.

[11] Patent Number: 4,873,366
[45] Date of Patent: Oct. 10, 1989

[54] PROCESS FOR PRODUCING 2,6-NAPHTHALENEDICARBOXYLIC ACID

[75] Inventors: Toshiharu Matsuda; Atsushi Sasakawa; Shoichiro Hayashi, all of Iwaki; Yutaka Konai, Machida, all of Japan

[73] Assignee: Kureha Kagaku Kogyo Kabushiki Kaisha, Tokyo, Japan

[21] Appl. No.: 177,774

[22] Filed: Apr. 5, 1988

[30] Foreign Application Priority Data

Apr. 7, 1987 [JP] Japan ................................. 62-85198

[51] Int. Cl.$^4$ ............................................ C07C 51/265
[52] U.S. Cl. .................................... 562/416; 562/417; 562/488
[58] Field of Search ................. 562/412, 416, 417, 488

[56] References Cited

U.S. PATENT DOCUMENTS 4,709,088 11/1987 Hirose et al. ....................... 562/414
4,716,245 12/1987 Hirose ................................. 562/416

FOREIGN PATENT DOCUMENTS 60-89445 5/1985 Japan .
60-89446 5/1985 Japan .
61-246143 11/1986 Japan .
246144 11/1986 Japan .

Primary Examiner—Werren B. Lone
Assistant Examiner—Vera C. Clarke
Attorney, Agent, or Firm—Oblon, Spivak, McClelland, Maier & Neustadt

[57] ABSTRACT

Disclosed in the present invention is a process for producing 2,6-naphthalenedicarboxylic acid comprising oxidizing 2,6-diisopropylnaphthalene or its partially oxidized intermediate with molecular oxygen in a solvent containing at least 50% by weight of an aliphatic monocarboxylic acid, having not more than three carbon atoms, in the presence of a catalyst composed of (i) a heavy metal comprising cobalt and/or manganese and (ii) bromine, and a salt of an inorganic acid having an acid dissociation constant Ka smaller than $1.34 \times 10^{-5}$ (at 25° C.) and a vapor pressure lower than that of the aliphatic monocarboxylic acid used as the solvent. According to the process of this invention, 2,6-naphthalenedicarboxylic acid of high bulk density can be obtained in a high yield and with high purity.

2 Claims, No Drawings

PROCESS FOR PRODUCING 2,6-NAPHTHALENEDICARBOXYLIC ACID

BACKGROUND OF THE INVENTION

The present invention relates to a process for producing, in a high yield and with high purity, 2,6-naphthalenedicarboxylic acid of high bulk density which is used for the preparation of polyesters such as polyethylene naphthalate and polyamides useful as a starting material for the production of films and synthetic fibers.

As methods for producing 2,6-naphthalenedicarboxylic acid (hereinafter referred to as "2,6-NDCA"), processes which 2,6-dimethylnaphthalene, 2,6-diethylnaphthalene or 2,6-diisopropylnaphthalene (hereinafter referred to as 2,6-DIPN) is oxidized with molecular oxygen in an acetic acid as a solvent, in the presence of a catalyst composed of cobalt and/or manganese and bromine are already known. (Refer to Japanese Patent Publication Nos. 43,893 (1973), 21,027 (1981), 2,223 (1983), 13,495 (1984), and 27,318 (1973); and Japanese Patent Application Laid-Open (KOKAI) Nos. 34,153 (1973), 42,654 (1974), 17,453 (1977), 89,445 (1985) and 89,446 (1985). Especially noticeable are the process in which 2,6-DIPN or its partially oxidized intermediate is oxidized with molecular oxygen in a solvent containing at least 50% by weight of an aliphatic monocarboxylic acid having not more than three carbon atoms in the presence of a catalyst composed of a heavy metal, comprising cobalt and/or manganese, and bromine, said heavy metal being used in an amount of at least 0.2 mole to one mole of 2,6-DIPN or its partially oxidized intermediate [Japanese Patent Application Laid-Open (KOKAI) No. 89,445 (1985)] and the process in which 2,6-DIPN or its partially oxidized intermediate is oxidized with molecular oxygen in a solvent containing at least 50% by weight of an aliphatic monocarboxylic acid having not more than three carbon atoms in the presence of a catalyst composed of a heavy metal, comprising cobalt and/or manganese, and bromine, said heavy metal being used in an amount of at least 1% by weight based on the solvent [Japanese Patent Application Laid-Open (KOKAI) No. 89,446 (1985)].

However, as a result of the studies on side reaction in the production of 2,6-NDCA by oxidizing 2,6-DIPN, the present inventors found out that the main side reactions are the following two reactions: (1) a cleaving reaction of the naphthalene nucleus to form trimellitic acid and (2) a polycondensation reaction. These side reactions can be suppressed to a certain extent by using a large amount of a heavy metal catalyst, comprising cobalt and/or manganese, but use of expensive cobalt or manganese in a large amount is undesirable. Also, the crystals of 2,6-NDCA obtained by using a large amount of the heavy metal catalyst are low in bulk density and is difficult to separate by filtration and, further, when dried, they are severely dusty and their transportation by belt conveyors, etc. is difficult.

The catalysts usable in the reaction for producing 2,6-NDCA by oxidizing 2,6-DIPN can largely be classified in two groups, i.e., cations and anions. As to cations, the effect of heavy metal ions such as cobalt and manganese ions and alkali metal ions such as sodium and potassium ions have been discussed [Japanese Patent Application Laid-Open (KOKAI) Nos. 246,143 (1986) and 246,144 (1986)], but as to anions, only the catalytic effect of bromine is known and no substantial studies have been made on the effect of anions.

The object of this invention is to provide a process manufacturing 2,6-NDCA having high bulk density, easy to treat and in a high yield by suppressing formation of by-product, that is, polycondensate which is common in a conventional processes.

SUMMARY OF THE INVENTION

In an aspect of the present invention, there is provided a process for producing 2,6-NDCA, which comprises oxidizing 2,6-DIPN or its partially oxidized intermediate with molecular oxygen in a solvent containing at least 50% by weight of an aliphatic monocarboxylic acid, having not more than three carbon atoms, in the presence of a catalyst composed of (i) a heavy metal comprising cobalt and/or manganese and (ii) bromine, and a salt of an inorganic acid having an acid dissociation constant Ka smaller than $1.34 \times 10^{-5}$ (at 25° C.) and a vapor pressure lower than that of an aliphatic monocarboxylic acid used as the solvent.

DETAILED DESCRIPTION OF THE INVENTION

The present invention relates to a process for producing 2,6-NDCA which comprises oxidizing 2,6-DIP or its partially oxidized intermediate with molecular oxygen in a solvent containing at least 50% by weight of an aliphatic monocarboxylic acid having not more than three carbon atoms in the presence of a catalyst composed of (i) a heavy metal comprising cobalt and/or manganese and (ii) bromine, and a salt of an inorganic acid having an acid dissociation constant Ka smaller than $1.34 \times 10^{-5}$ (at 25° C.) and a vapor pressure lower than that of the aliphatic monocarboxylic acid.

The starting material used in the present invention is 2,6-DIPN or its partially oxidized intermediate. The term "partially oxidized intermediate" used in the present invention means the substance which is produced by partial oxidation of 2,6-DIPN and can be 2,6-NDCA when further oxidized in the reaction system.

More precisely, the starting material of this invention is represented by the following formula (I):

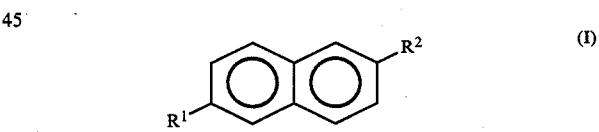

(I)

wherein $R^1$ is a group selected from the group consisting of

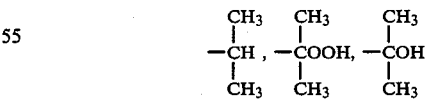

and $COCH_3$, and $R^{22}$ is a group selected from the group consisting of

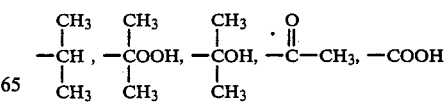

and $-CHO$, and $R^1$ and $R^2$ can be same or different from each other.

In the present invention, (i) cobalt and/or manganese and (ii) bromine are used as oxidation catalyst. The cobalt and manganese can be used as inorganic compounds such as oxides, hydroxides, carbonates and halides and as salts of organic acids such as formic acid, acetic acid, propionic acid, naphthenic acid and aromatic carboxylic acids. The bromine can be used as organic and inorganic compounds, provided that they are soluble in the oxidation reaction system and capable of producing $Br^-$ ions and more specifically, molecular bromine, inorganic compounds of bromine such as hydrogen bromide, hydrobromides, etc., and organic compounds of bromine such as methyl bromide, ethyl bromide, bromoform, ethylene bromide, alkyl bromide and bromoacetates can be used.

The catalytic effect of bromine has been well known for a long time, but there has been no discussion about the effect of anions other than bromine. The present inventors have found out that certain kinds of anions other than bromine ion have a remarkable activity to reduce a proton concentration in aliphatic monocarboxylic acids or to suppress the side reactions, epecially polycondensation reaction by coordinating with the cobalt or manganese compound. The compounds capable of producing anions having such effect are salts of inorganic acids having an acid dissociation constant Ka smaller than $1.34 \times 10^{-5}$ (at 25° C.) and a vapor pressure lower than that of an aliphatic monocarboxylic acid used as the solvent, such salts being soluble in the solvent under oxidation reaction conditions of 2,6-DIPN. Examples of such salts of inorganic acids are sodium tetraborate, ammonium tetraborate, potassium tetraborate, sodium molybdate, sodium phosphate, disodium hydrogenphosphate, etc. It is understood that the presence of the anions is, by regulating the redox potential of the cobalt and/or manganese compounds and especially suppressing the polycondensation reaction of 2,6-DIPN, to increase the yield of 2,6-NDCA. Furthermore, the anions have an important effect to give the 2,6-NDCA crystals of high bulk density by accelerating a crystal growth.

In the process of this invention, similar to a conventional process of manufacturing 2,6-NDCA, the catalyst, cobalt and/or manganese, is added in an amount of 0.005 to 0.15 gram atoms per 100 g of the solvent containing at least 50% by weight of an aliphatic monocarboxylic acid having not more than three carbon atoms and bromine is added in an atomic ratio of 0.05 to 0.5 to the cobalt and/or manganese. Further, a salt of an inorganic acid described above is added in an amount of 0.01 to 5 gram mols, preferably 0.05 to 1 gram mol per 1 gram atom of the cobalt and/or manganese, and after adjusting the pressure and temperature of the reaction system to the prescribed levels by introducing nitrogen gas, 2,6-DIPN or its partially oxidized intermediate is supplied to the reaction system, followed by flowing of a predetermined amount of oxygen to carry out oxidation of the starting material under pressure. The same oxidation conditions as used in the conventional processes can be applied. Generally, the higher the partial pressure of oxygen is, the faster proceeds the reaction, but from the practical standpoint, it is enough to set the partial pressure of oxygen not less than 0.1 $kg/cm^2$-abs., preferably around 0.2 to 8 $kg/cm^2$-abs. When oxygen is used in admixture with an inert gas, the reaction can proceed quickly to give 2,6-NDCA in a high yield even when the total pressure is below 30 $kg/cm^2$-G. The reaction may proceed even at around 60° C., but such low temperature is not economically advisable because of low reaction rate. On the other hand, a temperature over 220° C. increases formation of by-products, resulting in a low yield of 2,6-NDCA. The preferred reaction temperature is usually in the range of 80° to 220° C., more preferably 160° to 200° C. The process of the present invention can be performed according to any of batchwise, half-continuous and continuous reaction systems. In a conventional process, a yield of 2,6-NDCA is greatly affected by an amount of the catalyst, cobalt and/or manganese, used. For example, as shown in the Comparative Examples given later, when cobalt acetate tetrahydrate and manganese acetate tetrahydrate each in an amount of about 60 g to 1,500 g of the solvent, acetic acid, is used, the yield of 2,6-NDCA according to the conventional processes is around 60 mol% and when about 90 g of cobalt acetate tetrahydrate and about 280 g of manganese acetate tetrahydrate are used, the yield of 2,6-NDCA is around 80 mol%. On the other hand, in the process of the present invention, salt of a specific inorganic acid mentioned above is added and a yield of 2,6-NDCA of around 80 mol% can be achieved even when about 60 g of cobalt acetate tetrahydrate and about 60 g of manganese acetate tetrahydrate is used. This indicates that the process of the present invention can remarkably decreases the necessary amount of cobalt and managanese in comparison with the conventional processes.

According to the process of the present invention, when a salt of an inorganic acid, having an acid dissociation constant Ka smaller than $1.34 \times 10^{-5}$ (at 25° C.) and a vapor pressure lower than that of the aliphatic monocarboxylic acid used as the solvent, coexists with a heavy metal catalyst (cobalt and/or manganese) and bromine in the reaction system oxidizing 2,6-DIPN to 2,6-NDCA, the high-yield production of 2,6-NDCA having higher bulk density and better precipitability than those obtainable with the conventional processes becomes possible. For example, as illustrated in the Examples given later, the bulk density of 2,6-NDCA obtained from the conventional process (Comparative Examples 1 to 5) is 0.72 to 0.78 $g/cm^3$ while the bulk density of 2,6-NDCA obtained by the process of the present invention is 0.85 to 0.96 $g/cm^3$ (Examples 1 to 4). Further, according to the process of the present invention, it is possible to reduce the necessary amount of cobalt and/or manganese as compared with the necessary amount to give the same yields of 2,6-NDCA without a salt of an inorganic acid described above.

The present invention will be explained more in detail while referring to the following non-limitative Examples.

EXAMPLE 1

1,500 g of acetic acid, 62.3 g of cobalt acetate tetrahydrate, 62.3 g of manganese acetate tetrahydrate, 75 g of water, 15 g of ammonium bromide and 19.1 g of sodium tetraborate decahydrate were introduced into a 5-liter titanium-made autoclave. The mixture was pressurized to 15 $kg/cm^2$-G by a flow of nitrogen gas, heated to 180° C. under vigorous stirring and nitrogen gas flow was replaced by air flow of a rate of 860 Nl/hr. Into the autoclave, 212 g of 2,6-DIPN was introduced continuously over a period of 105 minutes under an air flow and air was blown in another one hour to complete the oxidation. After the reaction was over, air was replaced again by nitrogen gas and the reaction mixture was cooled to 100° to 105° C., hot filtered and washed with hot acetic acid and the precipitated 2,6-NDCA was separated. The yield of 2,6-NDCA was 76.4 mol%, its bulk density was 0.95 g/ml and the trimellitic acid yield was 11.4 mol%.

EXAMPLE 2

The oxidation reaction was performed in the same manner as in Example 1 except that the amount of sodium tetraborate decahydrate was changed to 38.2 g from 19.1 g.

EXAMPLE 3

The oxidation reaction was performed in the same manner as in Example 1 except that 26.3 of ammonium tetraborate tetrahydrate was used in place of 19.1 g of sodium tetraborate decahydrate.

EXAMPLE 4

The oxidation reaction was performed in the same manner as in Example 1 except that 24.2 g of sodium molybdate dihydrate was used in place of 19.1 g of sodium tetraborate decahydrate and the reaction was performed at 200° C. instead of 180° C.

COMPARATIVE EXAMPLE 1

The oxidation reaction was performed in the same manner as in Example 1 provided that no sodium tetraborate decahydrate as a salt of an inorganic acid was used.

COMPARATIVE EXAMPLE 2

The oxidation reaction was performed in the same manner as in Example 1 except that 16.4 g of sodium acetate was used in place of sodium tetraborate as a salt of an inorganic acid.

COMPARATIVE EXAMPLE 3

The oxidation reaction was performed in the same manner as in Example 1 except that 96 g of cobalt acetate tetrahydrate, 283.5 g of manganese acetate tetrahydrate were used and no sodium tetraborate decahydrate as a salt of an inorganic acid was used.

COMPARATIVE EXAMPLE 4

The oxidation reaction was performed in the same manner as in Example 1 except that 77.1 g of ammonium acetate was used in place of sodium tetraborate decahydrate.

COMPARATIVE EXAMPLE 5

The oxidation reaction was performed in the same manner as in Example 1 except that 98.1 g of potassium acetate was used in place of sodium tetraborate decahydrate as a salt of an inorganic acid.

All the results of Examples and Comparative Examples were shown in Table 1.

TABLE 1

| | Starting Material | | | | | | | | Reaction condition | | Results | | |
| | | | | | | | Salt of inorganic acid | | | | | Yield of trimel- | Bulk density |
| | | | Cobalt acetate | Manganese acetate | Bromide | | | | | | Yield of 2,6- | litic | of 2,6- |
| | Acetic Acid | Water | tetra-hydrate | tetra-hydrate | Com- | Amount | Com- | Amount | Temp. | Pres. kg/cm$^2$ | NDCA | acid | NDCA |
| No. | (g) | (g) | (g) | (g) | pound | (g) | pound | (g) | (°C.) | -G | (%) | (%) | (g/cm$^3$) |
|---|---|---|---|---|---|---|---|---|---|---|---|---|---|
| Ex. 1 | 1,500 | 75 | 62.3 | 62.3 | NH$_4$Br | 15 | Na$_2$B$_4$O$_7$·10H$_2$O | 19.1 | 180 | 15 | 76.4 | 11.4 | 0.95 |
| Ex. 2 | 1,500 | 75 | 62.3 | 62.3 | NH$_4$Br | 15 | Na$_2$B$_4$O$_7$·10H$_2$O | 38.2 | 180 | 15 | 86.3 | 10.6 | 0.96 |
| Ex. 3 | 1,500 | 75 | 62.3 | 62.3 | NH$_4$Br | 15 | (NH$_4$)$_2$B$_4$O$_7$·4H$_2$O | 26.3 | 180 | 15 | 80.6 | 11.0 | 0.96 |
| Ex. 4 | 1,500 | 75 | 62.3 | 62.3 | NH$_4$Br | 15 | Na$_2$MoO$_4$·2H$_2$O | 24.2 | 200 | 15 | 82.0 | 11.2 | 0.85 |
| Comp. Ex. 1 | 1,500 | 75 | 62.3 | 62.3 | NH$_4$Br | 15 | — | — | 180 | 15 | 63.3 | 12.6 | 0.78 |
| Comp. Ex. 2 | 1,500 | 75 | 62.3 | 62.3 | NH$_4$Br | 15 | NaOAc | 16.4 | 180 | 15 | 65.0 | 12.5 | 0.73 |
| Comp. Ex. 3 | 1,500 | 75 | 96 | 283.5 | NH$_4$Br | 15 | — | — | 180 | 15 | 80.2 | 9.5 | 0.75 |
| Comp. Ex. 4 | 1,500 | 75 | 62.3 | 61.4 | NH$_4$Br | 97.9 | NH$_4$OAc | 77.1 | 180 | 15 | 44.2 | 15.0 | 0.73 |
| Comp. Ex. 5 | 1,500 | — | 62.3 | 61.4 | KBr | 119 | KOAc | 98.1 | 180 | 15 | 75.0 | 12.0 | 0.72 |

What is claimed is:

1. A process for producing 2,6-naphthalenedicarboxylic acid which comprises oxidizing 2,6-diisopropylnaphthalene or its partially oxidized intermediate with molecular oxygen in a solvent containing at least 50% by weight of an aliphatic monocarboxylic acid having not more than three carbon atoms in the presence of a catalyst composed of
   (i) a heavy metal comprising cobalt, manganese or their mixture, and
   (ii) bromine, and a salt of an inorganic acid, having an acid dissociation constant Ka smaller than $1.34 \times 10^{-5}$, at 25° C., and a vapor pressure lower than that of said aliphatic monocarboxylic acid used as the solvent, which is selected from the group consisting of sodium tetraborate, ammonium tetraborate, potassium tetraborate, sodium molybdate, sodium phosphate, and disodium hydrogen phosphate.

2. The process according to claim 1, wherein said salt of an inorganic acid is sodium tetraborate, ammonium tetraborate, potassium tetraborate or sodium molybdate and is used in an amount of 0.01 to 5 gram moles per 1 gram atom of cobalt, manganese or their mixture.

* * * * *